US008137978B2

(12) United States Patent
Ford

(10) Patent No.: US 8,137,978 B2
(45) Date of Patent: Mar. 20, 2012

(54) DIAGNOSTIC METHOD FOR BIOMARKERS OF ADVERSE CORONARY EVENTS

(75) Inventor: David A. Ford, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 223 days.

(21) Appl. No.: 12/580,666

(22) Filed: Oct. 16, 2009

(65) Prior Publication Data

US 2011/0091980 A1   Apr. 21, 2011

(51) Int. Cl.
*G01N 33/92* (2006.01)
(52) U.S. Cl. ............ 436/71; 436/63; 436/124; 436/128; 436/129; 436/131
(58) Field of Classification Search .................... 436/57, 436/63, 71, 124, 128, 129, 131
See application file for complete search history.

(56) References Cited

U.S. PATENT DOCUMENTS 7,560,227 B2 * 7/2009 Kim et al. .................... 435/4
2011/0124031 A1 * 5/2011 Hazen et al. .................. 435/29

OTHER PUBLICATIONS

Baldus et al. Circulation, vol. 108, Sep. 2, 2003, oages 1440-1445.*
Albert et al. The Journal of Biological Chemistry, vol. 277, No. 7, Feb. 15, 2002, pp. 4694-4703.*
Albert et al. Journal of Chromatography B, vol. 877, 2009, pp. 2768-2777.*
Antonino Buffon, MD, Luigi M. Biasucci, MD, Giovanna Liuzzo, MD, Giuseppe D'Onofrio, MD, Filippo Crea, MD, Attilio Maseri, MD, Widespread Coronary Inflammation in Unstable Angine, The New England Journal of Medicine, Jul. 4, 2002, 5-12, vol. 347, No. 1, USA.
Arun K. Thukkani, Bradley D. Martinson, Carolyn J. Albert, George A. Vogler, David A. Ford, Neutrophil-mediated accumulation of 2-CIHDA during myocardial infarction: 2-CIDHA-mediated myocardial injury, American Journal of Physiology, Jan. 28, 2005, H2955-H2964, vol. 288, USA.
Arun K. Thukkani, Carolyn J. Albert, Kristin R. Wildsmith, Maria C. Messner, Bradley D. Martinson, Fong-Fu Hsu, David A. Ford, Myeloperoxidase-derived Reactive Chloinating Species from Human Monocytes Target Plasmalogens in Low Density Lipoprotein, The Journal of Biological Chemistry, Sep. 19, 2003, 36365-36372, v. 278, No. 38, USA.
Arun K. Thukkani, Fong-Fu Hsu, Jan R. Crowley, Robert B. Wysolmerski, Carolyn J. Albert, David A. Ford, Reactive Chlorinating Species Produced During Neutrophil Activation Target Tissue Plasmalogens, The Journal of Biological Chemistry, Feb. 8, 2002, 3842-3849, v. 277, No. 6, USA.
Arun K. Thukkani, Jane McHowat, Fong-Fu Hsu, Marie-Luise Brennan, Stanley L. Hazen, David A. Ford, Identification of a-Chloro Fatty Aldehydes and Unsaturated Lysophosphatidylcholine Molecular Species in Human Atherosclerotic Lesions, Circulation, Aug. 18, 2003, 3128-3133, retrieved from www.circulationaha.org, USA.
B Nikppor, G Turecki, C Fournier, P. Theroux, G.A. Rouleau, A Functional Myeloperoxidase Polumorphic Variatn is Associated with Coronary Artery Disease in French-Canadians, American Heart Journal, 2001, 336-339, vol. 142.
Baohai Shao, Abderrazzaq Belaaouaj, Christophe L. M. J. Verlinde, Xiaoyun Fu, Jay W. Heinecke, Methionine Sulfoxide and Proteolytic Cleavage Contribute to the Inactivation of Cathepsin G by Hypochlorous Acid, The Journal of Biological Chemistry, Aug. 12, 2005, 29311-29321, vol. 280, No. 32, USA.
Carolyn J. Albert, Jan R. Crowley, Fong-Fu Hsu, Arun K. Thukkani, David A. Ford, Reactive Chlorinating. Species Produced by Myeloperoxidase Target the Vinyl Ether Bond of Plasmalogens, The Journal of Biological Chemistry, Jun. 29, 2001, 23733-23741, v. 276, No. 26, USA.
Cem Gabay, MD and Irving Kushner, MD, Acute-phase Proteins and Other Systemic Responses to Inflammation, The New England Journal of Medicine, Feb. 11, 1999, 448-454, vol. 340, No. 6, USA.
D. Kutter, P. Devaquet, G. Vanderstocker, J.M. Paulus, V. Marchal, A. Gothot, Consequences of Total and Subtotal Mywloperoxidase Deficiency: Risk or Benefit?, Acta Haematologica, 2000, 10-15, vol. 104.
G.D. Reynolds and R.P. Vance, C-reactive Protein Immunohistochemical Localization in Normal and Atherosclerotic Human Aortas, Archives of Pathology & Laboratory Medicine, 1987, 265-269, vol. 111.
I.J. Kullo, G.T. Gau, A.J. Tajik, Novel Risk Factors for Atherosclerosis, Mayo Clinic Proceedings, 2000, 369-380, vol. 75.
John Danesh, Rory Collins, Paul Appleby, Richard Peto, Association of Figrinogen, C-reactive Protein, Albumin, or Leukocyte Count with Coronary Heart Disease, Journal of American Medical Association, May 13, 1998, 1477-1482, vol. 279, No. 18, retrieved Jun. 25, 2009 from www.jama.com.
Kristin R. Wildsmith, Carolyn J, Albert, Dhanalakshmi S. Anbukumar, David A. Ford, Metabolism of Myeloperoxidase-derived 2-Chlorohexadecanal, The Journal of Biological Chemistry, Jun. 23, 2006, 16849-16850, vol. 281, No. 25, USA.
Kristin R. Wildsmith, Carolyn J. Albert, Dhanalakshmi S. Anbukumar, David A. Ford, Metabolism of Myeloperoxidase-derived 2-Chlorohexadecanal, Journal of Biological Chemistry, Jun. 23, 2006, 16849-16860, v. 281, No. 25, USA.
Maria C. Messner, Carolyn J. Albert, David A. Ford, 2-Cholorhexadecanal and 2-Cholorhexadecanoic Acid Induce COX-2 Expression in Human Coronary Artery Endothelial Cells, LIPDS, Mar. 11, 2008, 8 pgs, AOCS, Springer.
Michelle A. Albert, Ellie Danielson, Nader Rifai, Paul M. Ridker, Effect of Statin Therapy on C-Reactive Protein Levels: The Pravastatin Inflammation/CRP Evalution (Prince): A Randomized Trial and Cohort Study, Journal of American Medical Association, Jul. 4, 2001, 64-74, vol. 286, No. 1, retrieved Jun. 25, 2009 from www.jama.com.

(Continued)

*Primary Examiner* — Maureen Wallenhorst
(74) *Attorney, Agent, or Firm* — Mark E. Stallion; Husch Blackwell LLP

(57) ABSTRACT

A diagnostic method using biomarkers to predict future adverse coronary events is provided. More particularly, the present invention is directed to diagnostic tests for characterizing an individual's risk of developing or having cardiovascular disease. In certain embodiments, the method of the present invention quantitates the presence of elevated levels of chlorinated lipids derived from myeloperoxidase as a prognostic indicator of future adverse coronary events.

18 Claims, 14 Drawing Sheets

OTHER PUBLICATIONS

Paul M. Ridker, Role of inflammatory biomarkers in prediction of coronary heart disease, The Lancet, Sep. 22, 2001, 946-948, vol. 358, USA.

R. Pecoits-Filho, P. Stenvinkel, A. Marchlewska, O. Heimburger, P. Barany, C. M. Hoff, C. J. Holmes, M. Suliman, B. Lindholm, M. Schalling, L. Nordfors, A Functional Variant of the Myeloperoxidase gene is Associated with Cardiovascular Disease in End-Stage Renal Disease Patients, Kidney International- Supplement, 2003, s172-176.

R. Vlaicu, H.G. Rus, F. Niculescu, A. Cristea, Immunoglobulins and Complement Components in Human Aortic Atherosclerotic Intima, Atherosclerosis, 1985, 35-50, vol. 55.

Ramachandran S. Vasan, MD., Biomarkers of Cardiovascular Disease Molecular Basis and Practical Considerations, Circulation, 2006, 2335-2362, retrieved from www.circulationaha.org, USA.

Renliang Zhang, Md, PhD, Marie-Luise Brennan, PhD, Ziaoming Fu, MS, Ronnier J. Aviles, MD, Gregory L. Pearce, MS, Marc S. Penn, MD, PhD, Eric J. Topol, MD, Dennis L. Sprecher, MD, Stanley L. Hazen, MD, PhD, Association Between Myeloperoxidase Levels and Risk of Cornoary Artery Disease, Journal of American Medical Association, Nov. 7, 2001, 2136-2142, v. 286, No. 17, USA.

S.S. Bassuk, N. Rifai, P.M. Ridker, High-sensitivity C-reactive Protein: Clinical Importance, Current Problems in Cardiology, 2004, 439-493, vol. 29.

Seigo Sugiyaman, Yoshikatsu Okada, Galina K. Sukhova, Renu Virmani, Jay W. Heinecke, Peter Libby, Macrophage Myecloperoxidase Regulation by Granulocyte Macrophage Colony-Stimulating Factor in Human Atherosclerosis and Implications in Acute Coronary Syndromes, American Journal of Pathology, Mar. 2001, v. 158, No. 3, USA.

Stephan Baldus, MD, Christopher Heeschen, MD, Thomas Meinertz, MD, Andreas M. Zeiher, MD, Jason P. Eiserich, PhD, Thomas Munzel, MD, Maarten L. Simoons, MD, Christian W. Hamm, MD, Myeloperoxidase Serum Levels predict Risk in Patients with Acute Coronary Syndromes, Retrieved from www.circulationaha.org, Jul. 10, 2003, 1440-1445, USA.

X. Fu, S.Y. Kassim, W.C. Parks, J.W. Heineck, Hypocholorous Acid Generated by Myeloperoxidase Modifies Adjacent Tryptophan and Glycine Residues in the Catalytic Domain of Matrix Metalloproteinase-7 (Matrilysin): An Oxidative Mechanism for Restraining Proteolytic Activity During Inflammation, Journal of Biological Chemistry, 2003, 28403-28409, vol. 278.

Pol et al., *J. Neuro. Anethesiology*, vol. 4(1), pp. 26-30 (1992).

McCabe, J. Ped Surgery, vol. 36(2), pp. 334-337 (Feb. 2001).

Nguyen et al., J. Physiol, vol. 565(2), pp. 403-413 (2005).

Ma et al., Amer. Heart Assoc., vol. 114(11) (2006).

* cited by examiner

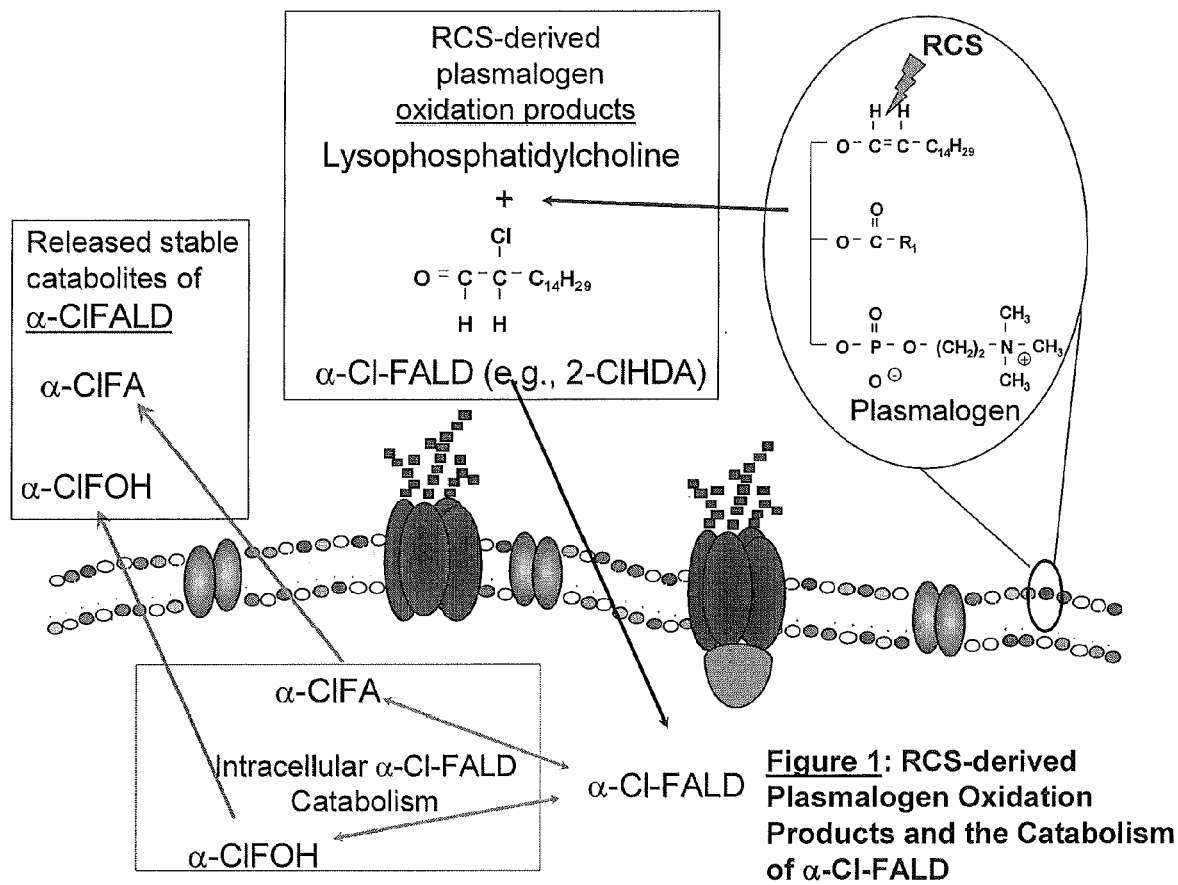
Figure 1: RCS-derived Plasmalogen Oxidation Products and the Catabolism of α-Cl-FALD

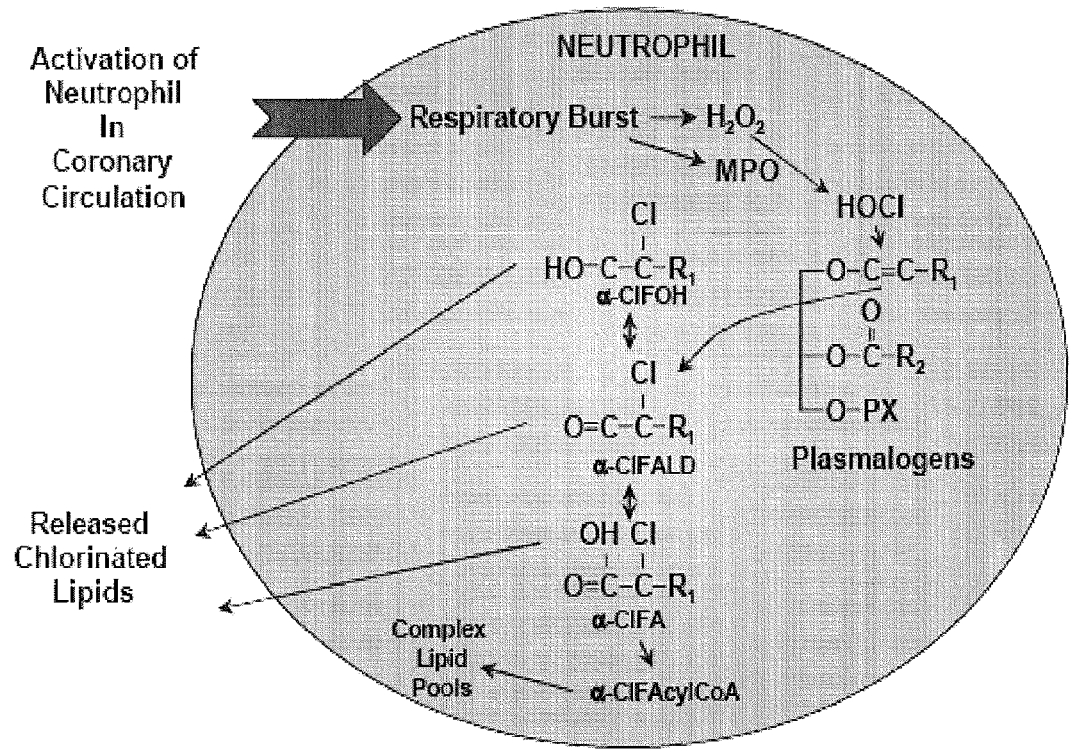
Figure 2: NOVEL METABOLIC PATHWAYS INITIATED BY ACTIVATED NEUTROPHILS: THE CHLORINATED LIPIDOME
α-ClFALD = α-chlorofatty aldehyde; α-ClFA = α-chlorofatty acid; α-ClFOH = α-chlorofatty alcohol

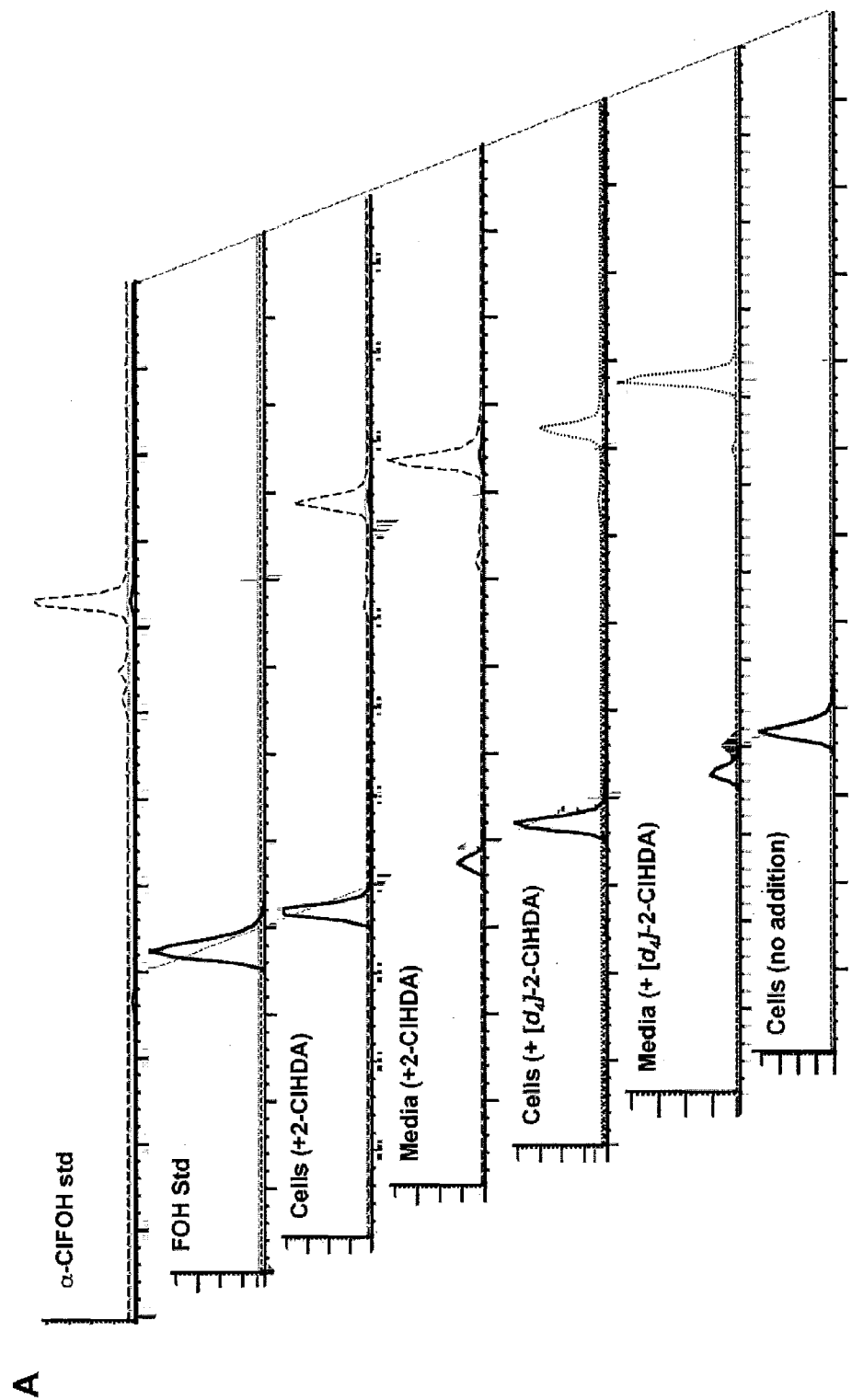
Figure 3: GC-MS Analyses of α-Chlorofatty Alcohol in Human Coronary Artery Endothelial Cells treated with 2-ClHDA and 2-Cl-[$d_4$]-HDA
α-ClFOH=α-chlorofatty alcohol; FOH=fatty alcohol; 2-ClHDA=2-chlorohexadecanal; 16:0-OH=hexadecanol; and 2-Cl-16:0-OH=2-chlorohexadecanol

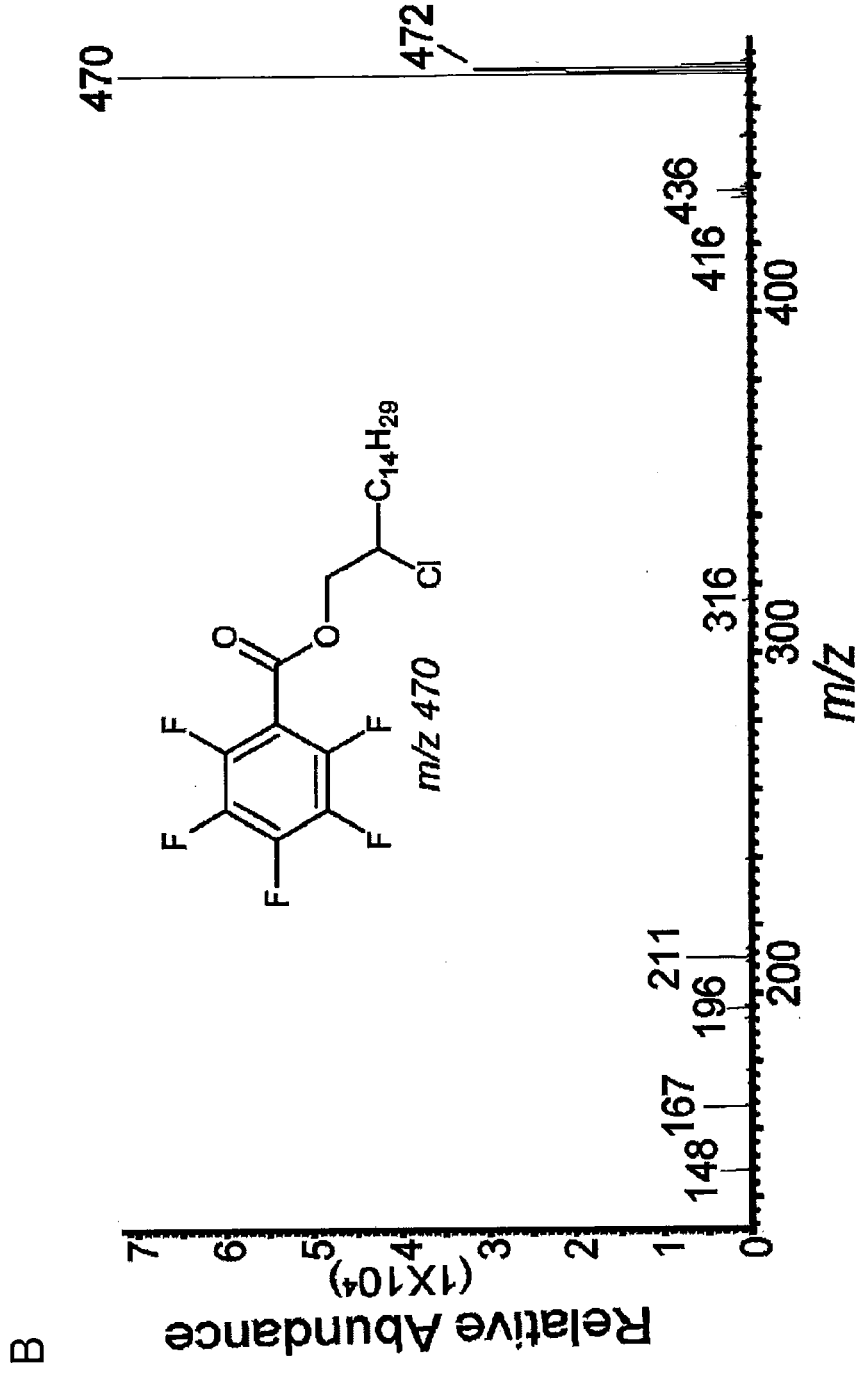
Figure 3: GC-MS Analyses of α-Chlorofatty Alcohol in Human Coronary Artery Endothelial Cells treated with 2-ClHDA and 2-Cl-[$d_4$]-HDA
α-ClFOH=α-chlorofatty alcohol; FOH=fatty alcohol; 2-ClHDA=2-chlorohexadecanal; 2-ClHDA=2-chlorohexadecanal; 16:0-OH=hexadecanol; and 2-Cl-16:0-OH=2-chlorohexadecanol

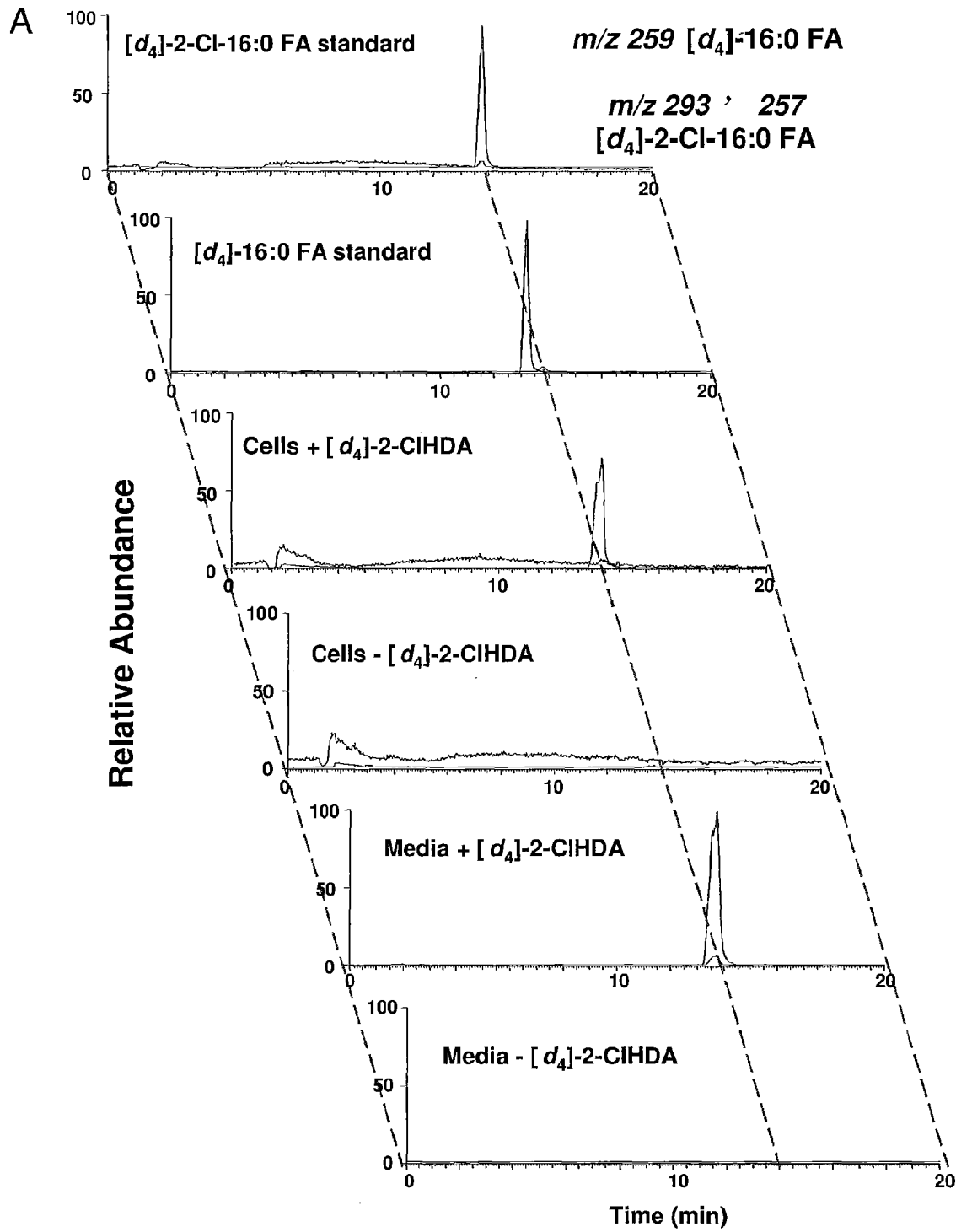
Figure 4: LC-MS Analyses of α-Chlorofatty Acid in Human Coronary Artery Endothelial Cells (HCAEC) treated with 2-Cl-[$d_4$]-HDA
2-ClHDA=2-chlorohexadecanal; 16:0-FA=hexadecanoic acid (palmitic acid); and 2-Cl-16:0-FA=2-chlorohexadecanoic acid (2-Cl-palmitic acid)

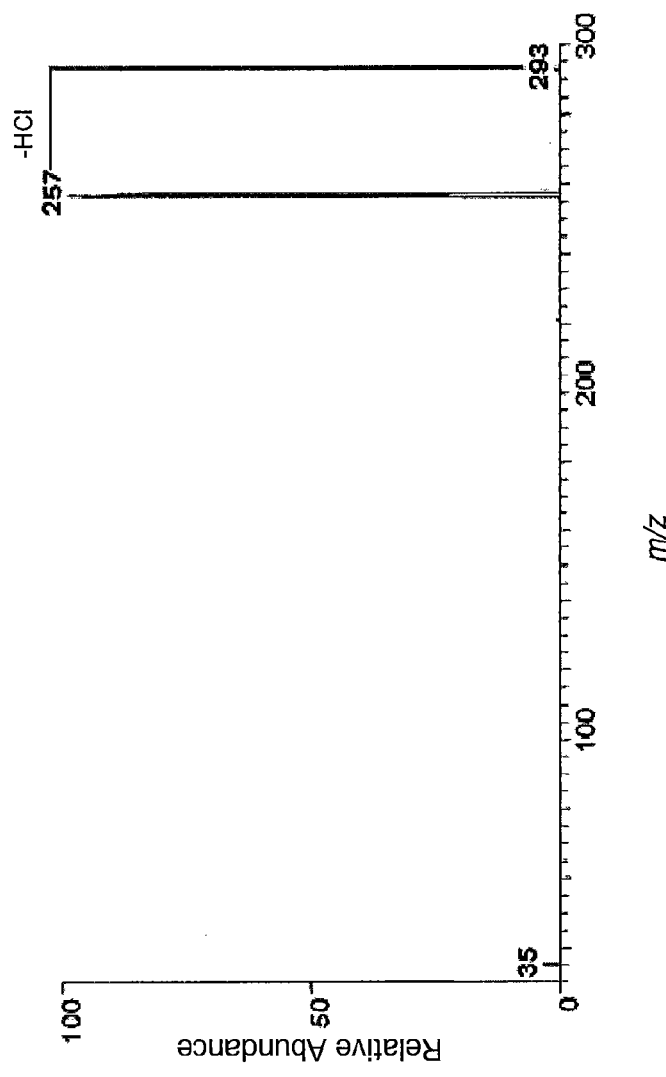
Figure 4: LC-MS Analyses of α-Chlorofatty Acid in Human Coronary Artery Endothelial Cells (HCAEC) treated with 2-Cl-[$d_4$]-HDA
2-ClHDA=2-chlorohexadecanal; 16:0-FA=hexadecanoic acid (palmitic acid); and 2-Cl-16:0-FA=2-chlorohexadecanoic acid (2-Cl-palmitic acid)

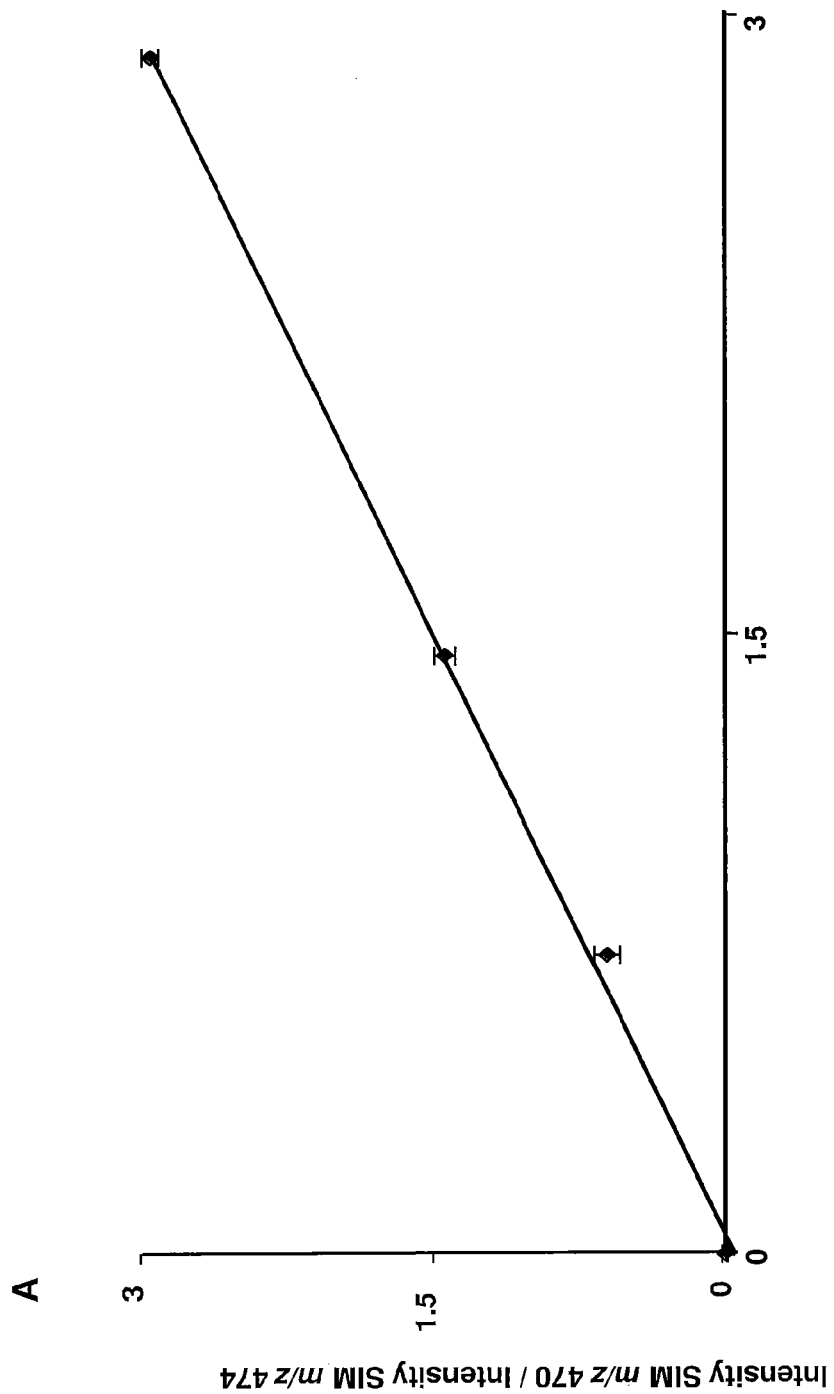
Figure 5: Standard Response Curves of 2-Cl-Hexadecanol (A) and 2-Cl-Hexadecanoic Acid (B) and their Deuterated Standards Using GC-MS and LC-MS, respectively.

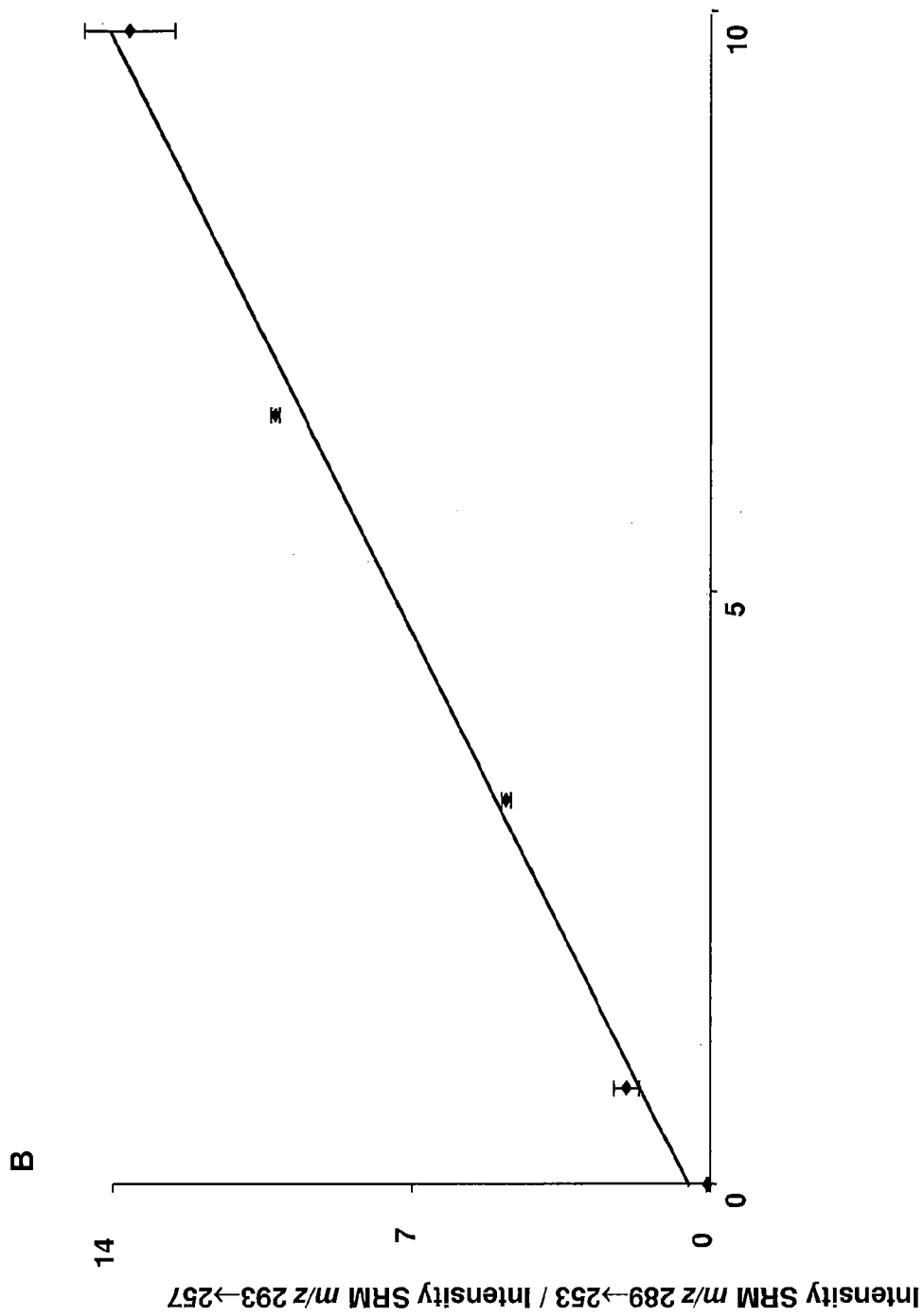
Figure 5: Standard Response Curves of 2-Cl-Hexadecanol (A) and 2-Cl-Hexadecanoic Acid (B) and their Deuterated Standards Using GC-MS and LC-MS, respectively.

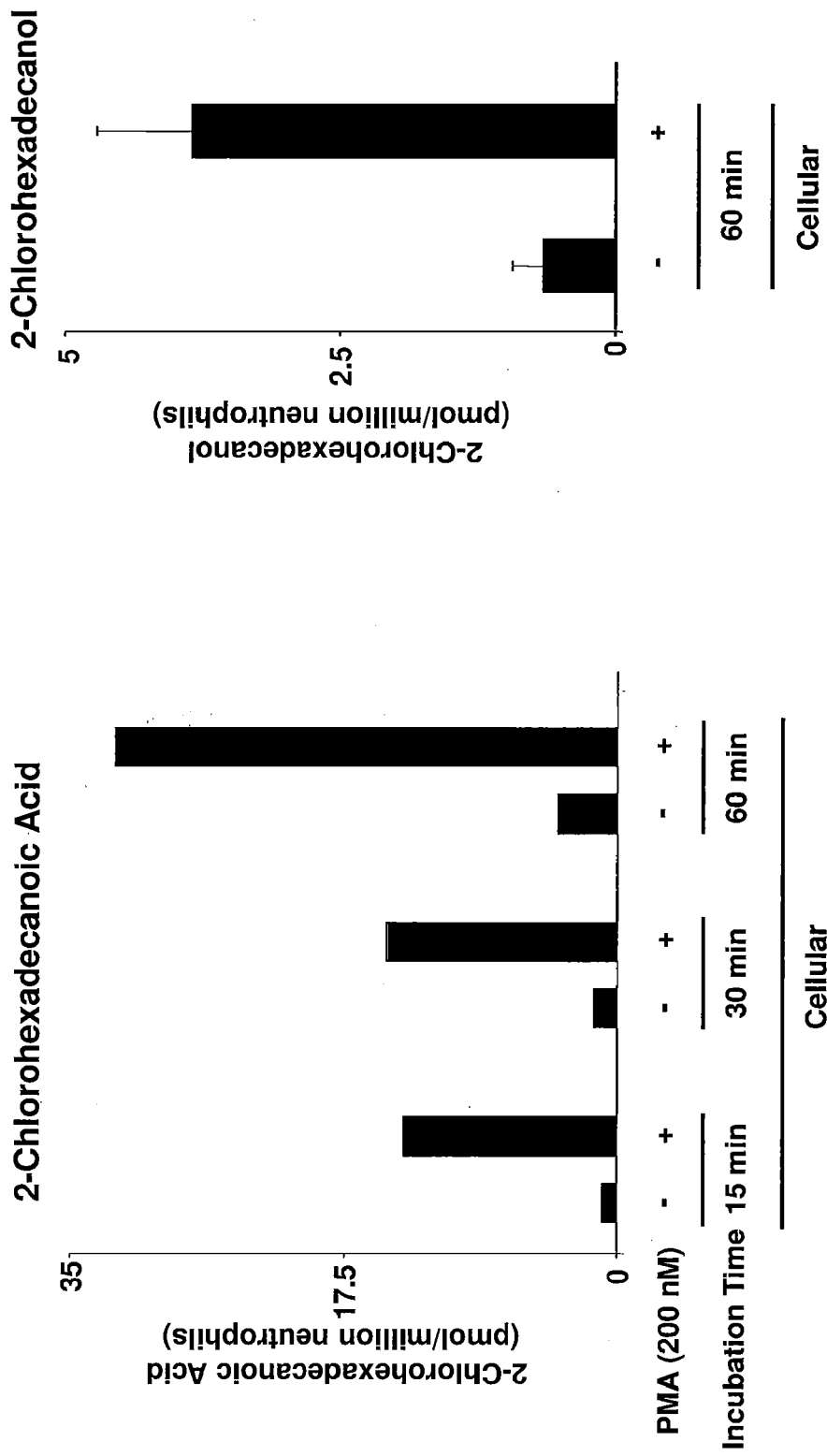
Figure 6: Phorbol Ester (PMA)-Stimulated 2-Chlorohexadecanoic Acid and 2-Chlorohexadecanol Production in Neutrophils

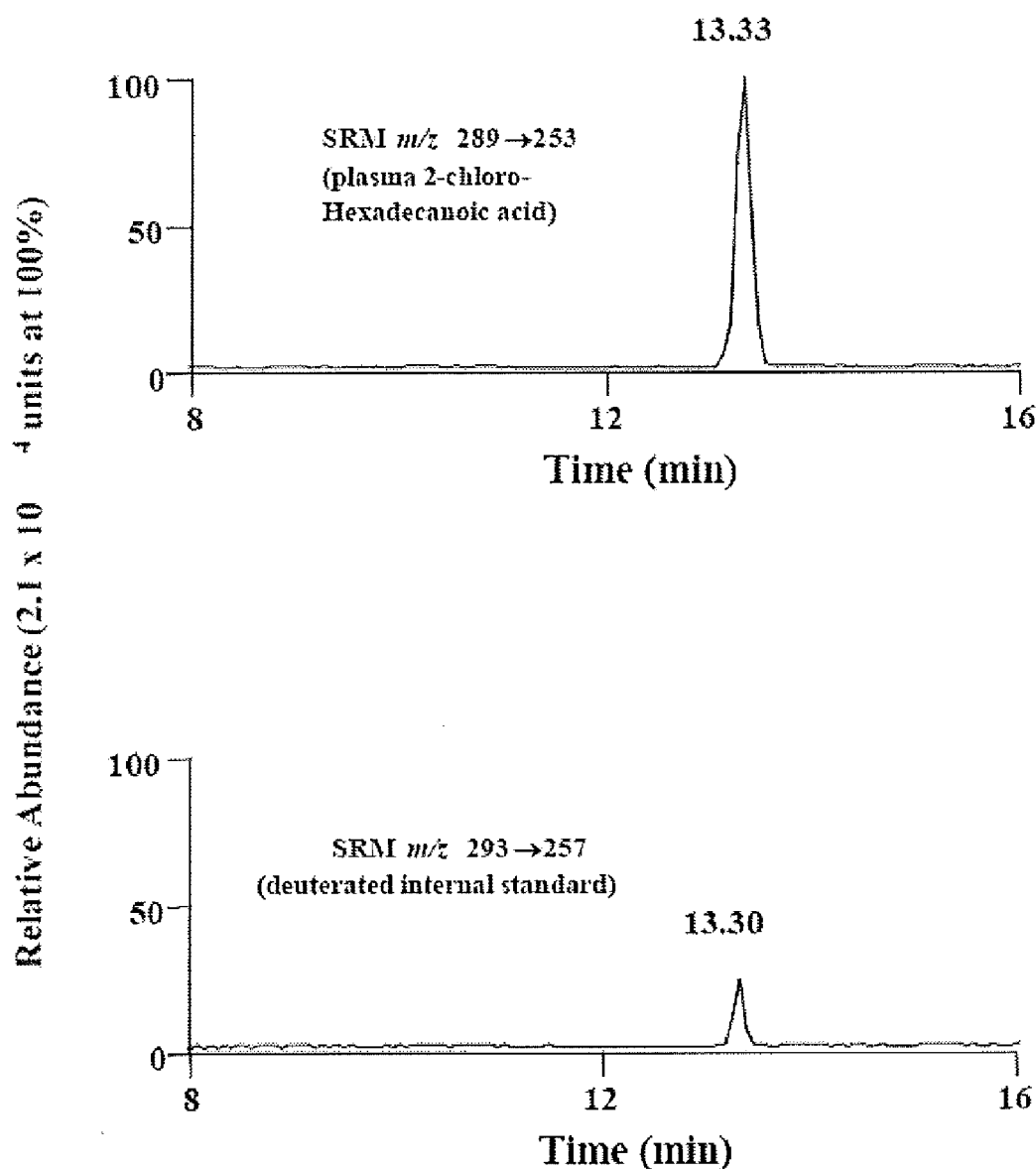
Figure 7 : LC-MS Analyses of 2-Chlorohexadecanoic Acid in Human Plasma Using Selected Reaction Monitoring Figure 8: PROCESSING AND CLEARANCE OF THE CHLORINATED LIPIDS
α-ClFALD = α-chlorofatty aldehyde; α-ClFA = α-chlorofatty acid; and α-ClFOH = α-chlorofatty alcohol
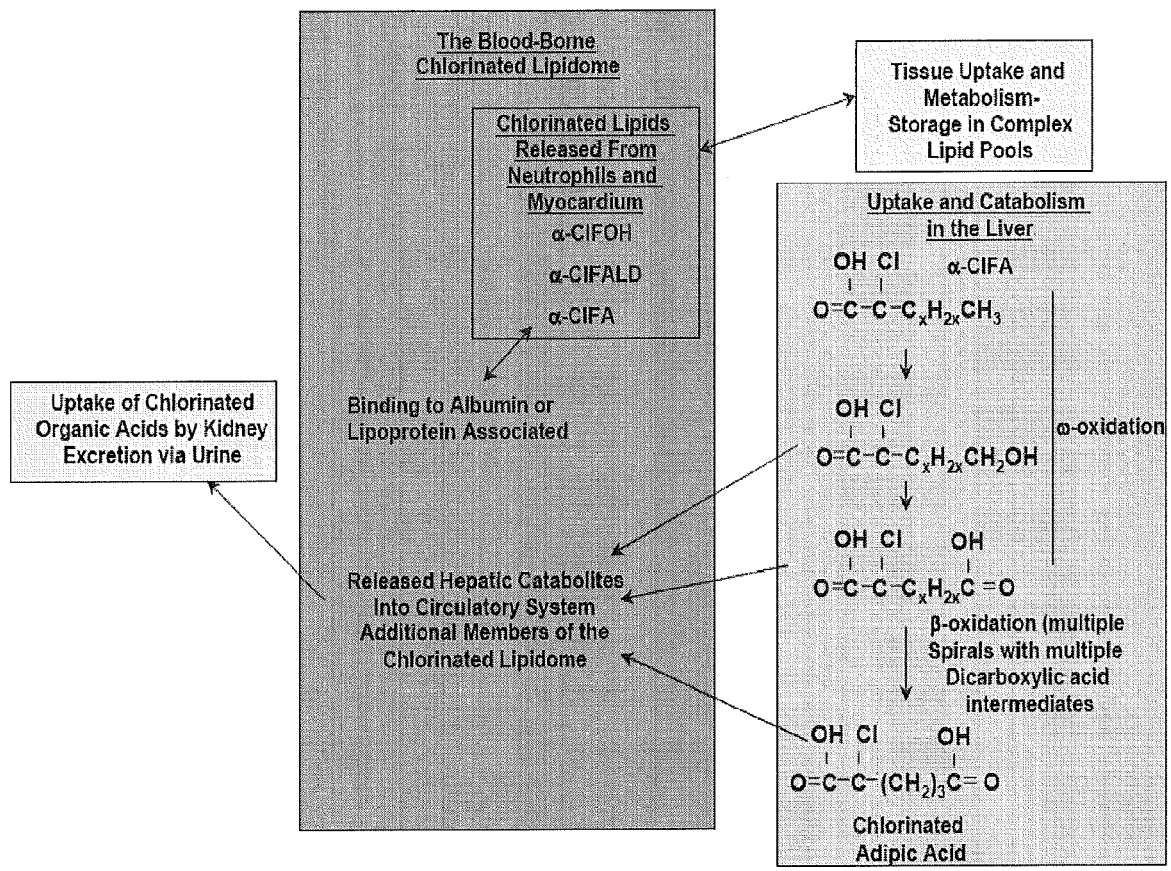

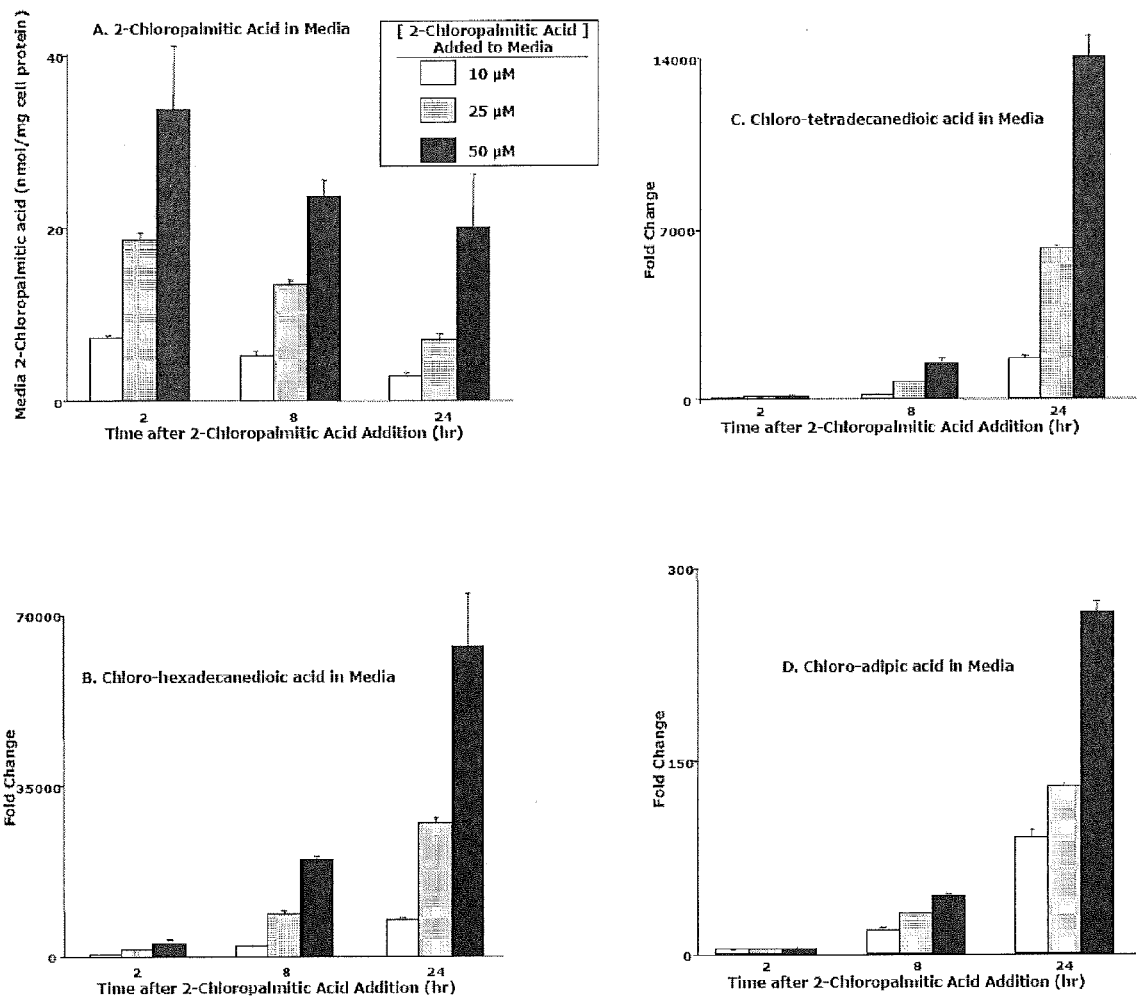
Figure 9: 2-Chloropalmitic Acid Metabolism by HepG2 cells

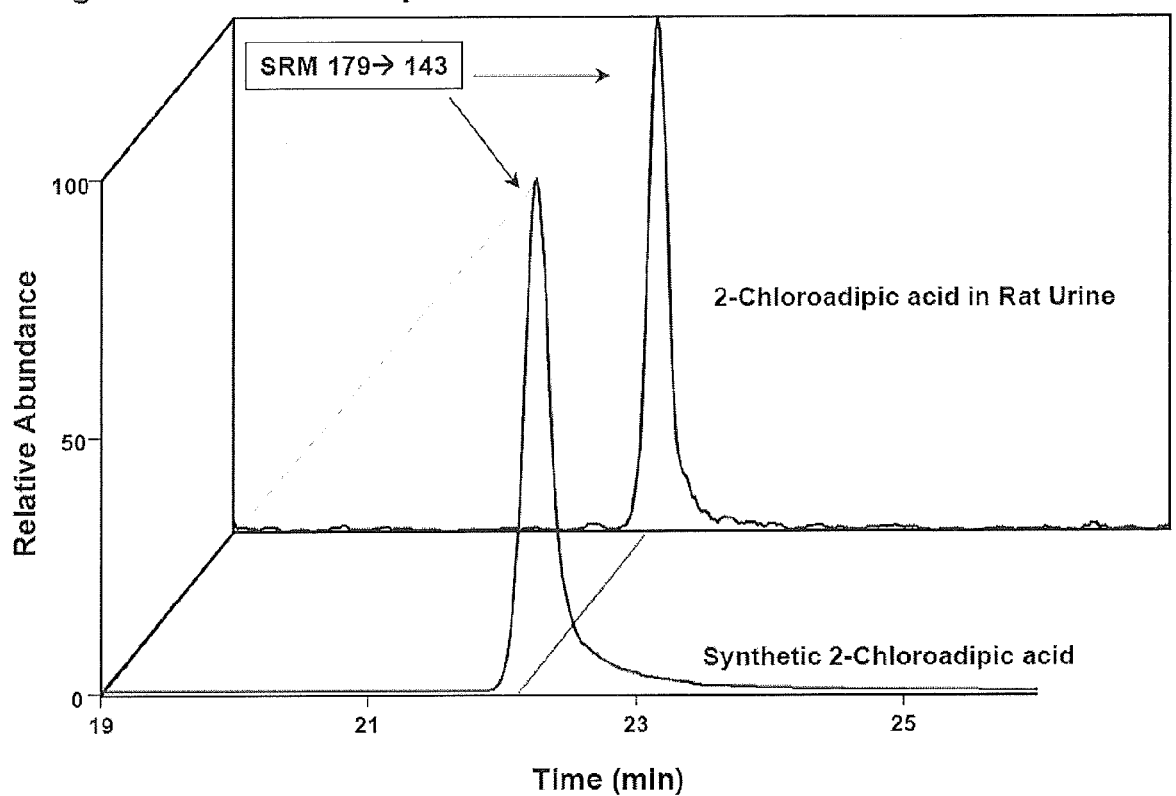

Figure 11 : Flow Injection of HepG2 Triglycerides with Electrospray Ionization Mass Spectrometry-Cells were treated 24 hrs with either no α-ClFA (Control) or 10 μM α-ClFA
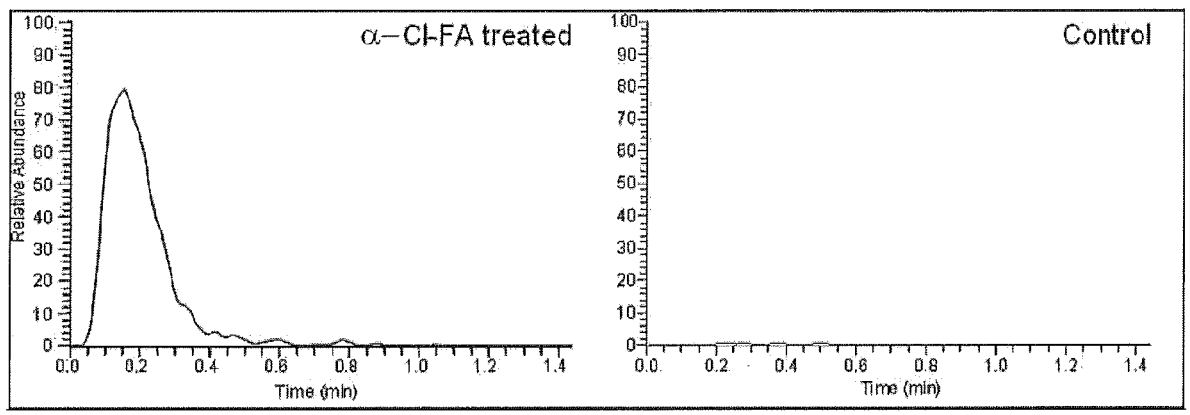
Figure 12
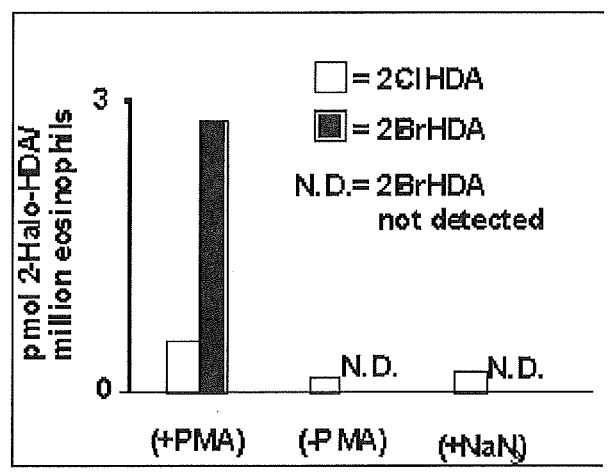

DIAGNOSTIC METHOD FOR BIOMARKERS OF ADVERSE CORONARY EVENTS

BACKGROUND OF THE INVENTION

A leading cause of death in the United States is heart disease. About one million persons in the United States die of heart disease each year. Heart disease is a combination of many diseases. The principal cause of heart disease is atherosclerosis which is a vascular disease that results in narrowing of the arteries that provide oxygen and nutrient-rich blood to the heart. When blood supply is diminished appreciably, the pain of angina pectoris may be felt. Such pain is frequently exacerbated when the heart requires an unusually large amount of blood such as during emotional stress or exercise. When the heart is thus deprived of its oxygen supply, heart muscle tissue dies. The narrowing of the blood vessels by atherosclerosis is anatomically caused by the accumulation of atherosclerotic plaques on the walls of the blood vessels. These plaques may rupture off of the lining of the blood vessel and occlude downstream blood vessels resulting in an acute adverse coronary event leading to sudden unpredicted fatalities associated with myocardial infarction and stroke. Accordingly, there exists a need in the art for a prognostic method to predict future risk of adverse coronary events.

Prognostic indicators of future adverse coronary events are known; however, each has its own inherent limitations. Two such indicators that are related to vascular inflammation are myeloperoxidase (MPO) and C-reactive protein (CRP). Plasma levels of MPO derived from circulating neutrophils have been found to correlate with cardiovascular disease and risk of major adverse coronary events. Neutrophils undergo degranulation within the coronary vasculature in acute coronary syndromes and MPO is a predominant protein in human neutrophils that is released during degranulation. Functional polymorphisms in the promoter region of MPO that result in decreased MPO expression have also been associated with decreased risk for cardiovascular disease. Blood and leukocyte levels of MPO serve as independent predictors of angiographically significant coronary artery disease. Recently, MPO has been shown to be a biomarker for risk of future cardiovascular events in patients with acute coronary syndromes. Since plasma MPO levels increase prior to elevations in plasma troponin T (TnT, a marker of myocardial cell death) levels, it has been suggested that MPO may be involved in the pathophysiological sequelae of acute coronary events. In fact, the identification of MPO in the shoulder region of atherosclerotic plaques has suggested MPO's role in plaque instability. Furthermore, oxidants produced by MPO have profound effects on the matrix metalloproteinases that functionally impact plaque stability. The prognostic value of MPO as an indicator of future coronary events and the biochemical mechanisms that MPO activity can have on plaque stability suggest that biomarkers indicative of MPO catalytic activity may improve the prediction of future coronary events. However, the use of MPO as a prognostic indicator is limited since the dynamic change in levels of MPO in the blood is only 1-2 fold and therefore does not allow for measurement of the catalytic or amplified response of MPO activity. Accordingly, there is a need in the art for a diagnostic method to predict future risk of adverse coronary events that is indicative of the catalytic or amplified response of MPO activity.

A second indicator of future adverse coronary events is C-reactive protein (CRP) which is an acute phase reactant and a sensitive, but non-specific marker, of inflammation that is enriched in atherosclerotic lesions. The use of CRP as a blood-borne marker that predicts CAD risk has become part of routine preventive risk assessment. However, a limitation of CRP as a blood-borne biomarker is the high incidence of false-positive results due to infections that are unrelated to cardiovascular disease. Accordingly, there is a need in the art for a specific biomarker of adverse coronary events that is not as easily influenced by other events such as infection that may falsely contribute to elevated levels of the indicator.

SUMMARY OF THE INVENTION

The present invention is generally directed to a diagnostic method of using biomarkers to predict future adverse coronary events. More particularly, the present invention is directed to diagnostic tests for characterizing an individual's risk of developing or having cardiovascular disease. In certain embodiments, the method of the present invention quantitates the presence of elevated levels of chlorinated lipids derived from myeloperoxidase as a prognostic indicator of future adverse coronary events.

BRIEF DESCRIPTION OF THE SEVERAL VIEWS OF THE DRAWING

The accompanying drawing forms a part of this specification and is to be read in conjunction therewith:

FIG. 1 is a schematic representation of reactive chlorinating species (RCS)-derived plasmalogen oxidation products and the catabolism of α-chlorofatty aldehyde;

FIG. 2 is a schematic representation of the metabolic pathways initiated by activated neutrophils;

FIG. 3A is a gas chromatography-mass spectrometry chromatogram of α-chlorofatty alcohol in human coronary artery endothelial cells treated with 2-ClHDA and 2-Cl-[$d_4$]-HDA;

FIG. 3B is a graphical representation of the mass spectrum of the pentafluorobenzoyl ester of α-ClFOH, 2-chlorohexadecanol;

FIG. 4A is a liquid chromatography-mass spectrometry chromatogram of stable isotope labeled fatty acid and α-ClFA;

FIG. 4B is a graphical representation of α-chlorofatty acid in human coronary artery endothelial cells treated with 2-Cl-[$d_4$]-HDA;

FIG. 5 is a graphical representation of the standard response curves of 2-Cl-hexadecanol (A) and 2-Cl-hexadecanoic Acid (B) and their deuterated standards using GC-MS and LC-MS, respectively;

FIG. 6 is a bar chart representation of phorbol ester-stimulated 2-chlorohexadecanoic Acid (A) and 2-chlorohexadecanol (B) production in neutrophils;

FIG. 7 is a liquid chromatography-mass spectrometry chromatogram of 2-chlorohexadecanoic acid (A) and its deuterated internal standard (B) in human plasma using selected reaction monitoring;

FIG. 8 is a schematic representation of the processing and clearance of chlorinated lipids;

FIG. 9 is a bar chart representation of 2-chloropalmitic acid metabolism by HepG2 cells;

FIG. 10 is a graphical representation of 2-chloroadipic acid in rat urine;

FIG. 11 is a graphical representation of the flow injection HepG2 triglycerides with electrospray ionization; and FIG. 12 is a bar chart representation of 2-bromohexadecanal metabolism.

DETAILED DESCRIPTION OF THE INVENTION

The present invention provides diagnostic methods for characterizing an individual's risk for developing or having an adverse coronary event. More particular, the present invention is generally directed to characterizing an individual's risk for developing or having an adverse coronary event by determining the presence of myeloperoxidase-derived chlorinated lipids in body fluids and tissues. In certain embodiments, the method hereof includes obtaining the level of chlorinated lipids in body tissues or fluids of a patient. In other embodiments, the method hereof includes identifying the molecular species of a chlorinated lipid in the body tissues or fluids of a patient. The level of chlorinated lipids or molecular species thereof present in the sample is then compared to a standard value to provide a risk value that characterizes the patient's risk of developing or having an adverse coronary event. The present invention also provides kits that include assays for determining the presence or levels of myeloperoxidase-derived chlorinated lipids in body tissues of fluids. It will be appreciated by those skilled in the art that the methods of the present invention disclosed herein may also serve as a screening test for similar diseases involving activated phagocytes and/or inflammation including, but not limited to, atherosclerosis, arthritis, ischemia/reperfusion injury, inflammatory bowel disease and similar inflammatory and vascular diseases.

The present invention is predicated upon the discovery that tissue plasmalogens are targeted by hypochlorous acid produced by activated neutrophil-derived myeloperoxidase (MPO). This reaction leads to the production of a family of chlorinated lipids useful in the diagnostic method of the present invention and that function as a better prognostic indicator of future adverse coronary events than either MPO or CRP. Chlorinated lipids are a catalytic product of MPO activity (i.e., one molecule of MPO can produce hundreds to thousands of molecules of chlorinated lipids) making their dynamic range in plasma much greater than that of MPO. Further, in comparison to CRP, chlorinated lipids are a much more specific marker of inflammation.

The mechanism responsible for the production of chlorinated lipids is shown in FIG. 1. In brief, MPO produces short-lived RCS that target tissue plasmalogens leading to the release of α-chlorofatty aldehyde (α-ClFALD) that can be either oxidized or reduced to α-chlorofatty acid (α-ClFA) or α-chlorofatty alcohol (α-ClFOH), respectively. Each of these classes (α-ClFA and α-ClFOH) can then be divided into several molecular species. The diversity of these classes and species present in a patient's blood can be used to draw conclusions of the site of their production (e.g., the coronary arteries) as well as the metabolic state of the heart (i.e., heart viability).

For example and in accordance with certain embodiments of the present invention, because there are differences in the molecular species of α-ClFALD released from human LDL and monocyte plasmalogen pools, differential increases in plasma molecular species of α-ClFA reflects a signature production and release of these MPO-generated metabolites from culprit vascular lesions responsible for acute coronary events. Changes in the plasma levels of α-ClFA and α-ClFOH reflects the oxidative status of the tissues at the sites of RCS production. For example, tissues that are targeted by RCS and that are incapable of α-ClFALD oxidation will release α-ClFOH while those cells capable of α-ClFALD oxidation will release α-ClFA. Thus, discrimination between these two oxidation state metabolites of α-ClFALD in the plasma enhances the predictive value of MPO and its oxidation products for clinical outcomes of patients with coronary artery disease.

Moreover, it is believed that increased plasma levels of α-ClFOH will precede that of plasma troponin T (TnT, a specific marker of heart injury/death), and thus may be an earlier marker of myocardial infarction prior to irreversible injury in a large lesion area. That is, alterations in cardiac respiratory status that would shunt α-ClFALD metabolism to α-ClFOH may precede terminal injury to the cell resulting in cell membrane damage accompanied by TnT release into plasma.

More particularly, α-chlorofatty aldehyde (α-ClFALD) was the first chlorinated lipid discovered in this family of lipids and is the biological precursor of other chlorinated lipids enumerated herein. α-ClFALD is produced as a result of MPO-generated RCS targeting the vinyl ether bond of plasmalogens. α-ClFALD accumulates in activated neutrophils, lipoproteins targeted by RCS generated from activated monocytes, human atherosclerotic lesions, and infarcted rat myocardium. Tissue specific profiles of plasmalogen molecular species are reflected in disparate molecular species of α-ClFALD that are released by RCS attack. For example, 2-chlorooctadecanal is the predominant α-ClFALD molecular species produced from RCS targeting LDL plasmalogen pools while 2-chlorohexadecanal is produced from RCS targeting monocyte plasmalogen pools. The accumulation of α-ClFALD at sites of inflammation, as well as in injured tissues of the cardiovascular system, suggests that these molecules may be an important mediator of host cell injury.

Moreover, α-ClFALD can be oxidized to α-chlorofatty acid (α-ClFA) or reduced to α-chlorofatty alcohol (α-ClFOH) as shown in FIG. 2. These chlorinated lipids, α-ClFA and α-ClFOH, are released from neutrophils and host tissues including the myocardium and can be detected in plasma as prognostic indicators of future adverse coronary events. There are also metabolites of α-ClFA that can be detected in urine that can serve as non-invasive (urine-borne) indicators of future adverse coronary events.

α-ClFALD and its Metabolites.

α-ClFOH and α-ClFA were shown to be metabolites of α-Cl-FALD by employing stable isotope labeling of human coronary artery endothelial cells (HCAEC) and mass spectrometric techniques. FIG. 3B shows the mass spectrum of the pentafluorobenzoyl (PFB) ester of the α-ClFOH, 2-chlorohexadecanol. The parent ion, m/z 470, is accompanied by an ion, m/z 472, that is approximately one-third its intensity, demonstrating that this is a monochlorinated molecule (due to the natural isotope abundance of $^{35}Cl$ and $^{37}Cl$ at a 3 to 1 ratio). The gas chromatography-mass spectrometry (GC-MS) chromatogram of this derivative is shown in FIG. 3A (α-ClFOH standard (std)) using selected ion monitoring (SIM) for m/z 470 and negative ion-chemical ionization. The PFB ester of 2-chlorohexadecanol is resolved from its non-halogenated analog (FOH standard, SIM m/z 436). HCAEC that are not treated with 2-ClHDA produce hexadecanol (e.g., m/z 436), but do not produce 2-chlorohexadecanol (e.g., m/z 470) as shown in FIG. 3A. In contrast, HCAEC that are treated with 2-ClHDA produce 2-chlorohexadecanol as well as hexadecanol (Cells+2-ClHDA, FIG. 3A). 2-Chlorohexadecanol is also released into the cell culture media in cells treated with 2-ClHDA (Media+2-ClHDA, FIG. 3A).

Additional experiments were performed with HCAEC that were labeled with stable isotope-labeled 2-ClHDA-[7,7,8,8-$d_4$]-2-chlorohexadecanal ([d4]-2-ClHDA). Only [$d_4$]-2-chlorohexadecanol (e.g., m/z 474), but not 2-chlorohexadecanol (e.g., m/z 470) or [$d_4$]-hexadecanol (e.g., m/z 440) were produced in HCAEC treated with [$d_4$]-2-ClHDA (Cells+[$d_4$]-2-ClHDA, FIG. 3A). [$d_4$]-2-chlorohexadecanol was also released into the cell culture media from these cells. Additionally, [$d_4$]-2-ClHDA treated HCAEC produced stable isotope labeled α-ClFA. FIG. 4 shows results from liquid chromatography-mass spectrometry (LC-MS) of stable isotope labeled fatty acid (FA) and α-ClFA. [d₄]-hexadecanoic acid was monitored by SIM of m/z 259 and [d₄]-2-chlorohexadecanoic acid was monitored by the selected reaction monitoring (SRM) transition from m/z 293 to 257 (loss of HCl) (e.g., FIG. 4B). Only cells treated with [d₄]-2-ClHDA produced [d₄]-2-chlorohexadecanoic acid, that was cell-associated as well as released into the media as shown in FIG. 4A. Taken together, stable isotope labeling experiments have demonstrated that α-ClFALD is metabolized by endothelial cells resulting in the production of α-ClFA and α-ClFOH. Furthermore, these stable isotope labeling experiments coupled with either LC-MS or GC-MS analyses have led to the methods of the present invention for the quantitation of α-ClFA and α-ClFOH in biological samples.

Further studies have shown that reactive brominating species (RBS), produced by either MPO- or EPO-released by activated neutrophil or eosinophil, respectively, target plasmalogens. GC-MS and proton NMR analyses showed that 2-bromohexadecanal (2-BrHDA) was produced from plasmalogens targeted by RBS. Bromide was the preferred substrate for eosinophil peroxidase and chloride was not appreciably used even at a 1000-fold molar excess. The potential physiological significance of this pathway was suggested by the demonstration that 2-BrHDA was produced by PMA-stimulated eosinophils (FIG. 12) and by the demonstration that 2-BrHDA is a phagocyte chemoattractant. 2-BrHDA is preferentially produced in PMA-stimulated eosinophils (+PMA) incubated in the presence of physiological concentrations of NaCl and NaBr (FIG. 12). Furthermore, in control experiments (−PMA) as well as in PMA-stimulated eosinophils in the presence of the peroxidase inhibitor, azide, 2-BrHDA was not produced (FIG. 12). Taken together, these studies demonstrate the targeting of the vinyl ether bond of plasmalogens by the RBS produced by eosinophil peroxidase and by activated eosinophils resulting in the production of brominated fatty aldehydes. These findings may have implications in eosinophilic heart disease as well as pulmonary disease and some cancers, which include eosinophil infiltrations.

In summary, MPO is known to be released from neutrophils prior to adverse coronary events. The enzymic product of MPO is HOCl that targets plasmalogens resulting in the release of the chlorinated lipid, α-ClFALD. α-ClFALD production is the rate limiting step for the production of a family of chlorinated lipid species derived from α-ClFALD. This family of lipids includes α-ClFA, α-ClFOH, α-chlorodicarboxylic acids (including α-chloroadipic acid) and α-ClFA esterified in triglyceride pools. These chlorinated lipid metabolites are produced in vivo, and their production is dependent on MPO activity. This panel of chlorinated lipid species can be used as prognostic indicators of future adverse coronary events.

EXAMPLES

The following examples are for purposes of illustration only and are not intended to limit the scope of the claims that are appended hereto.

Example 1

Quantitation of α-ClFA and α-ClFOH in biological samples.

Deuterated internal standards, 2-chloro-[d₄]-hexadecanoic acid and 2-chloro-[7,7,8,8-d₄]-hexadecanol were synthesized to enable quantification α-ClFA and α-ClFOH in biological samples using stable isotope dilution techniques. The response curves for natural chlorinated lipids and their deuterated analogs are shown in FIG. 5, which shows the linear response between the amount of natural and deuterated chlorinated lipid to the response of the mass spectrometers. Human neutrophils were treated with 200 nM phorbol ester (PMA, an activator of neutrophils resulting in increased MPO activity) for either 15, 30 or 60 min and compared to control-treated neutrophils. At the end of the treatments, neutrophil lipids were extracted in the presence of the internal standards for α-ClFA and α-ClFOH (2-chloro-[7,7,8,8-d₄]-hexadecanoic acid and 2-chloro-[7,7,8,8-d₄]-hexadecanol, respectively). The lipid extracts were then subjected to LC-MS with SRM m/z 289→253 for detection of 2-chlorohexadecanoic acid and SRM m/z 293→257 for detection of the internal standard 2-chloro-[d₄]-hexadecanoic acid.

Example 2

Additionally, lipid extracts were treated with pentafluorobenzoyl chloride to produce the fatty alcohol PFB ester derivatives that were subsequently subjected to GC-MS with negative ion-chemical ionization and SIM of m/z 470 for the PFB ester derivative of 2-chlorohexadecanol and SIM of m/z 474 for the PFB ester derivative of the internal standard 2-chloro-[d₄]-hexadecanol (e.g., see FIG. 3). FIG. 6 is a summary of the data from these experiments that shows the accumulation of α-ClFA (2-chlorohexadecanoic acid) and α-ClFOH (2-chlorohexadecanol) in PMA-activated neutrophils from 3 separate independent preparations and experiments.

Example 3

FIG. 7 shows the LC-MS analyses of α-ClFA using human plasma from one healthy donor. These data demonstrate the sensitivity of this method as well as the feasibility of the proposed studies. The upper tracing in FIG. 7 shows the SRM detection of 2-chlorohexadecanoic acid in plasma (peak at 13.33 min). The lower tracing in FIG. 8 shows the SRM detection of the internal standard, 2-chloro-[7,7,8,8-d₄]-hexadecanoic acid, that was added during lipid extraction of the plasma. In our preliminary analyses of eleven healthy humans, the plasma level of 2-chlorohexadecanoic acid is 1.6±0.2 fmol/μl of plasma (mean S.E.M.). α-ClFA production is dependent on MPO-catalyzed oxidation of lipids and α-ClFA is a stable blood-borne metabolite that can be used to monitor MPO-catalyzed oxidation as a prognostic indicator of future adverse coronary events. It should also be appreciated that a α-ClFOH levels may provide an enhanced prognostic evaluation of the scope of myocardial injury since its metabolism from α-ClFALD is dependent on the vitality of the myocardial tissue.

Example 4

Two other chlorinated lipids that have prognostic value are α-chloroadipic acid and α-ClFA that is complexed (stored) in triglyceride pools. α-ClFA is metabolized by either storage in triglyceride pools or is broken down in the liver (FIG. 8). In brief α-ClFA is omega oxidized to produce dicarboxylic acids that are shortened and eventually excreted in the urine. FIG. 9 shows the metabolites of 2-chloropalmitic acid by a transformed liver cell culture line, HepG2 cells. Panel A of FIG. 9 shows that over time 2-chloropalmitic acid added to the cell culture medium decreases in a time and concentration dependent manner. Concomitant with the loss of 2-chloropalmitic acid is the accumulation of the omega oxidation product, 2-chlorohexadecanedioc acid (Panel B of FIG. 9). Further metabolism of 2-chlorohexadecanedioc acid leads to 2-chlorotetradecanedioc acid (Panel C of FIG. 9) and eventually 2-chloroadipic acid (Panel D of FIG. 9). These metabolites were quantified using gas chromatography-mass spectrometry techniques employing conversion of the carboxylic acids and dicarboxylic acids to their pentafluorobenzyl ester derivatives and negative ion-chemical ionization mass spectrometry.

Example 5

The appearance of 2-chloroadipic acid as a metabolite of the α-ClFA, 2-chloropalmitic acid, is very important since short chain dicarboxylic acids such as adipic acid are excreted from the body in urine. FIG. 10 shows liquid chromatography-mass spectrometry tracings of authentic synthetic 2-chloroadipic acid and that of 2-chloroadipic acid present in rat urine. This technique exploits selected reaction monitoring 2-chloroadipic acid in a triple quadrupole mass spectrometer.

Example 6

α-ClFA is also metabolized by storing it in triglyceride pools in HepG2 cells. FIG. 11 shows flow injection analyses of triglycerides from HepG2 cells that have been treated in the presence and absence of α-ClFA. After 24 hrs, the lipids were extracted from these cells and the triglycerides were then purified by thin layer chromatography. These purified triglycerides were then subjected to flow injection analyses of two molecular species of triglyceride. The first species having a molecular ion at m/z 855 contains three fatty acids including two palmitic acid residues and one oleic acid residue. The other molecular ion at m/z 889 contains three fatty acids including one residue each of palmitic acid, 2-chloropalmitic acid, and oleic acid. There are also other combinations of fatty acids, including 2-chloropalmitic acid esterified in the triglyceride pool of the cells treated with α-ClFA. Since liver cells secrete the lipoproteins, such as HDL, VLDL/LDL that are circulating in the plasma, α-ClFA esterified to triglycerides are candidates as prognostic indicators of future adverse coronary events.

Having described the invention in detail, those skilled in the art will appreciate that modifications may be made of the invention without departing from the spirit and scope thereof. Therefore, it is not intended that the scope of the invention be limited to the specific embodiments described. Rather, it is intended that the appended claims and their equivalents determine the scope of the invention.

I claim:

1. A diagnostic method for characterizing inflammatory or vascular disease risk comprising the steps of:
   a) determining levels of chlorinated lipids in a biological sample from a test subject by comparing determined amounts of said chlorinated lipids to known amounts of standard deuterated chlorinated lipids, wherein said biological sample is selected from the group consisting of plasma, serum, blood, urine, and combinations thereof; and
   b) comparing said determined chlorinated lipid levels from said test subject to chlorinated lipid levels determined in healthy subjects; wherein elevated levels of said chlorinated lipids from said test subject as compared to said chlorinated lipid levels in healthy subjects indicate that the test subject is at risk for an inflammatory or vascular disease.

2. The method of claim 1, wherein said inflammatory or vascular disease is selected from the group consisting of atherosclerosis, arthritis, ischemia/reperfusion injury, and inflammatory bowel disease.

3. The method of claim 1, wherein said chlorinated lipid is a catalytic product of myeloperoxidase activity.

4. The method of claim 3, wherein said chlorinated lipid is α-chlorofatty aldehyde.

5. The method of claim 4 further comprising the step of discriminating between oxidation state metabolites of said a-chlorofatty aldehyde to enhance the predictive value of said chlorinated lipid levels.

6. The method of claim 5, wherein said oxidation state metabolites of said α-chlorofatty aldehyde are selected from the group consisting of α-chlorofatty acids, α-chlorofatty alcohols, α-chlorocarboxylic acids, α-chlorofatty acids esterified in triglyceride pools, and combinations thereof.

7. The method of claim 1, wherein said deuterated standard is selected from the group consisting of 2-chloro-[$d_4$]-hexadecanoic acid, 2-chloro[$7,7,8,8$-$d_4$]-hexadecanol, and combinations thereof.

8. The method of claim 1, wherein elevated levels of said chlorinated lipids precede release of plasma troponin from damaged cell membranes.

9. The method of claim 1 further comprising the step of assigning a risk value to said elevated levels of chlorinated lipids, wherein said risk value characterizes the test subject's risk of developing or having an inflammatory or vascular disease.

10. A diagnostic method for characterizing an adverse coronary event risk comprising the steps of:
   a) determining levels of chlorinated lipids in a biological sample from a test subject by comparing determined amounts of said chlorinated lipids to known amounts of standard deuterated chlorinated lipids, wherein the biological sample is selected from the group consisting of plasma, serum, blood, urine, and combinations thereof; and
   b) comparing said determined chlorinated lipid levels from said test subject to chlorinated lipid levels determined in healthy subjects; wherein elevated levels of said chlorinated lipids from said test subjects as compared to said chlorinated lipid levels in healthy subjects indicate that the test subject is at risk for an adverse coronary event.

11. The method of claim 10, wherein said chlorinated lipid is a catalytic product of myeloperoxidase activity.

12. The method of claim 11, wherein said chlorinated lipid is α-chlorofatty aldehyde.

13. The method of claim 12 further comprising the step of discriminating between oxidation state metabolites of said α-chlorofatty aldehyde to enhance the predictive value of said chlorinated lipid levels.

14. The method of claim 13, wherein said oxidation state metabolites of said α-chlorofatty aldehyde are selected from the group consisting of α-chlorofatty acids, α-chlorofatty alcohols, α-chlorocarboxylic acids, α-chlorofatty acids esterified in triglyceride pools, and combinations thereof.

15. The method of claim 10, wherein said deuterated standard is selected from the group consisting of 2-chloro-[$d_4$]-hexadecanoic acid, 2-chloro[$7,7,8,8$-$d_4$]-hexadecanol, and combinations thereof.

16. The method of claim 10, wherein elevated levels of said chlorinated lipids precede release of plasma troponin from damaged cell membranes.

17. The method of claim 10 further comprising the step of assigning a risk value to said elevated levels of chlorinated lipids, wherein said risk value characterizes the test subject's risk of developing or having an adverse coronary event.

18. A diagnostic method for characterizing a health risk comprising the steps of:
- a) determining levels of brominated lipids in a biological sample from a test subject by comparing determined amounts of said brominated lipids to known amounts of standard deuterated brominated lipids, wherein the biological sample is selected from the group consisting of plasma, serum, blood, urine, and combinations thereof; and
- b) comparing said determined brominated lipid levels from said test subject to brominated lipid levels determined in healthy subjects; wherein elevated levels of said brominated lipids from said test subjects as compared to said brominated lipid levels in healthy subjects indicate that the test subject is at risk for an adverse coronary event.

* * * * *